(12) United States Patent
Shackelford, Jr.

(10) Patent No.: US 12,053,206 B2
(45) Date of Patent: Aug. 6, 2024

(54) RETRACTABLE SURGICAL BLADE DEVICE AND METHOD

(71) Applicant: Howard L Shackelford, Jr., Wheeling, WV (US)

(72) Inventor: Howard L Shackelford, Jr., Wheeling, WV (US)

( * ) Notice: Subject to any disclaimer, the term of this patent is extended or adjusted under 35 U.S.C. 154(b) by 0 days.

(21) Appl. No.: 16/901,239

(22) Filed: Jun. 15, 2020

(65) Prior Publication Data
US 2020/0405340 A1 Dec. 31, 2020

Related U.S. Application Data

(60) Provisional application No. 62/866,282, filed on Jun. 25, 2019.

(51) Int. Cl.
*A61B 17/3211* (2006.01)
*A61B 17/00* (2006.01)

(52) U.S. Cl.
CPC ... *A61B 17/3211* (2013.01); *A61B 2017/0023* (2013.01); *A61B 2017/0042* (2013.01); *A61B 2017/00526* (2013.01); *A61B 2017/32113* (2013.01)

(58) Field of Classification Search
CPC ............ A61B 17/3211; A61B 17/3213; A61B 17/3215; A61B 17/3217; A61B 2017/0023; A61B 2017/0042; A61B 2017/00526; A61B 2017/32113; A61B 2017/32116
See application file for complete search history.

(56) References Cited

U.S. PATENT DOCUMENTS

| | | | | |
|---|---|---|---|---|
| 3,025,598 A | * | 3/1962 | Nissen | B26B 5/001 30/162 |
| 4,858,324 A | | 8/1989 | Wiech, Jr. | |
| 5,064,411 A | * | 11/1991 | Gordon, III | A61B 17/0493 2/2.5 |
| 5,207,696 A | * | 5/1993 | Matwijcow | A61B 17/3211 30/151 |
| 5,475,925 A | * | 12/1995 | Newman | B26B 5/001 30/162 |
| 5,531,754 A | * | 7/1996 | Shackelford, Sr. | A61B 17/3211 30/162 |

(Continued)

FOREIGN PATENT DOCUMENTS

EP 2367483 9/2011
WO 2018/207137 A1 11/2018

*Primary Examiner* — Jocelin C Tanner

(57) ABSTRACT

A retractable surgical blade includes a handle defining a channel and a surgical blade member. The surgical blade member includes a body to which is secured a surgical blade. The body has a portion which engages the channel so that the surgical blade member can move from a cutting position in which the surgical blade projects from the handle and can be employed in a surgical procedure to a retracted position in which the surgical blade is disposed in the channel. When in the retracted position, the surgical blade is unable to cut or stab persons associated with the surgical procedure. The device further includes cooperating locking members on the handle and the body to position the surgical blade member in the desired position. An associated method of performing a surgical procedure is also disclosed.

13 Claims, 3 Drawing Sheets

(56) References Cited

U.S. PATENT DOCUMENTS

| | | | |
|---|---|---|---|
| 6,015,419 A * | 1/2000 | Strome | A61B 17/3211 |
| | | | 606/167 |
| 6,254,621 B1 * | 7/2001 | Shackelford | A61B 17/3213 |
| | | | 30/162 |
| 6,353,204 B1 * | 3/2002 | Spaay | B23P 15/40 |
| | | | 219/121.72 |
| 7,647,704 B2 | 1/2010 | Petersen | |
| 8,181,352 B1 * | 5/2012 | Shackelford, Sr. | ......................... |
| | | | A61B 17/3215 |
| | | | 30/162 |
| 2004/0098004 A1 * | 5/2004 | George | A61B 17/3211 |
| | | | 606/167 |
| 2004/0163262 A1 | 8/2004 | King et al. | |
| 2009/0007436 A1 * | 1/2009 | Daskal | H01L 21/68764 |
| | | | 30/346 |
| 2013/0158585 A1 * | 6/2013 | O'Brien | A61B 17/3209 |
| | | | 606/172 |
| 2014/0142600 A1 * | 5/2014 | Kumar | A61B 17/3211 |
| | | | 606/167 |
| 2017/0281213 A1 * | 10/2017 | Early | A61B 17/320016 |
| 2019/0125487 A1 * | 5/2019 | Fatiny | A61C 3/02 |

\* cited by examiner

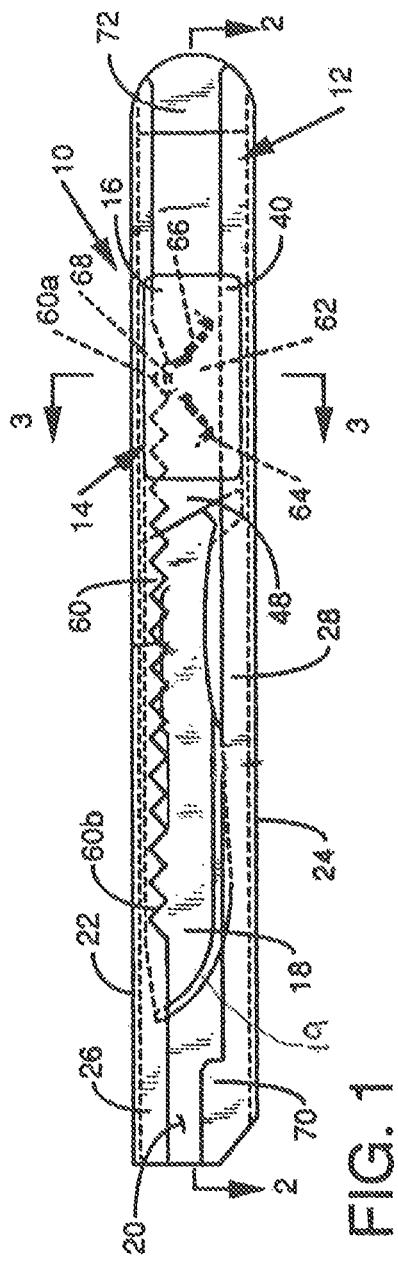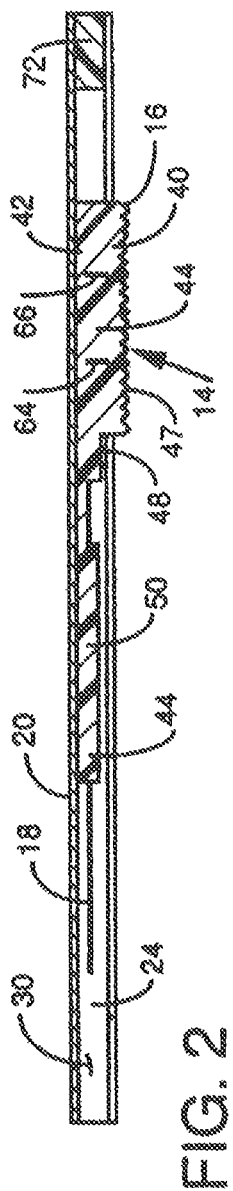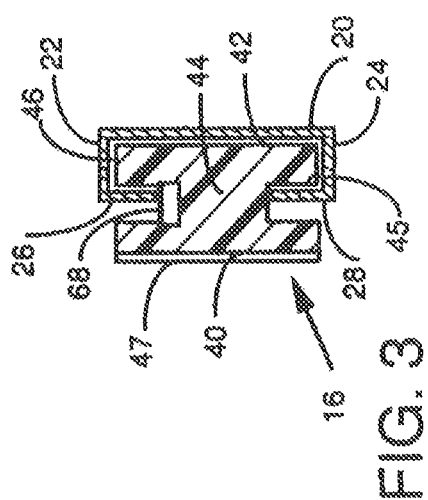

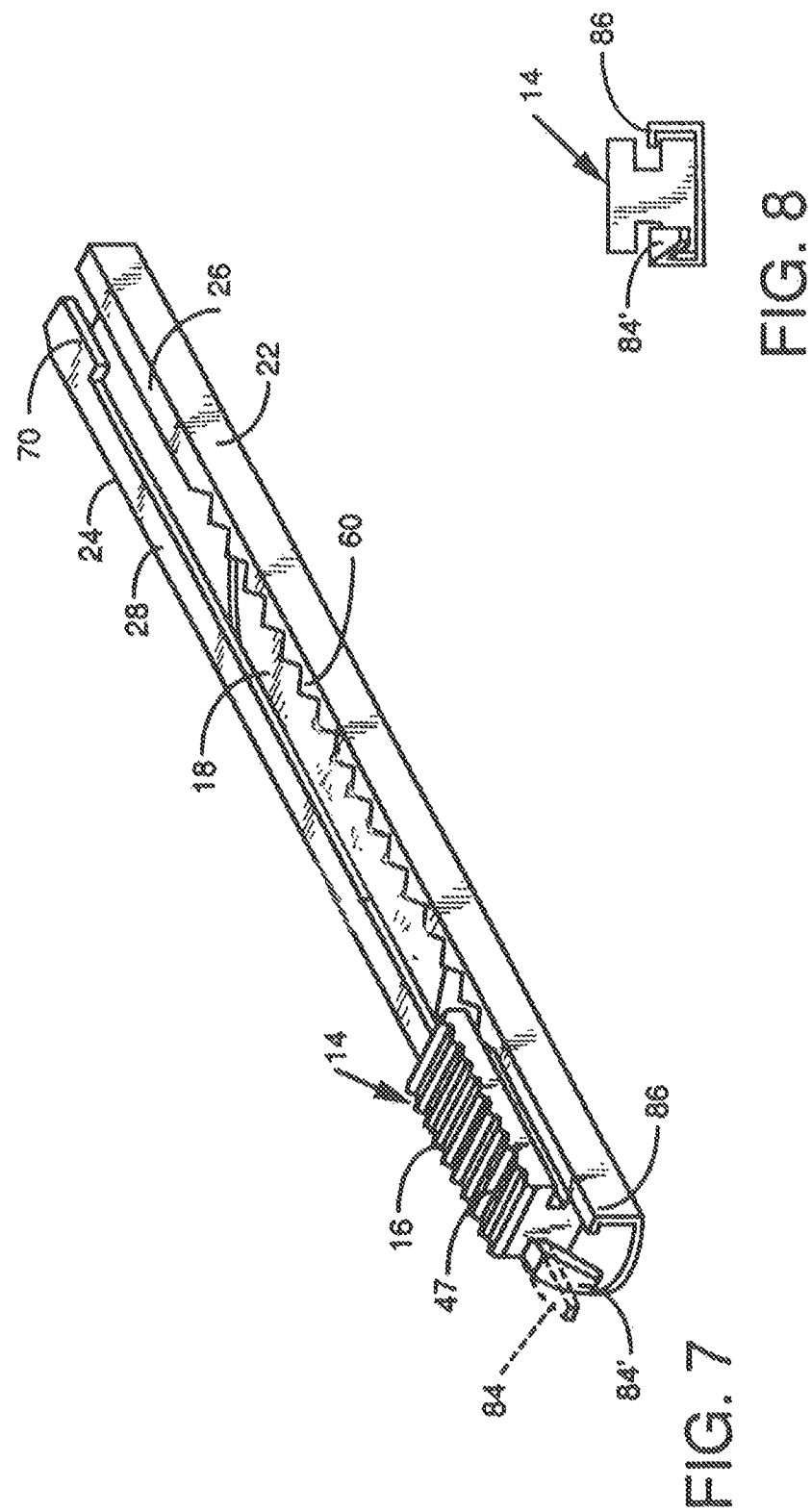

RETRACTABLE SURGICAL BLADE DEVICE AND METHOD

CROSS-REFERENCE TO RELATED PATENT APPLICATIONS

This patent application claims the benefit of U.S. Provisional Application No. 62/866,282 filed Jun. 25, 2019, entitled "RETRACTABLE SURGICAL BLADE DEVICE AND METHOD", which is hereby incorporated by reference.

BACKGROUND

The application generally relates to a retractable surgical blade device and an associated method The application relates more specifically to a retractable surgical plastic blade device with a slider member having an integral blade portion and an associated method for manufacture and use.

Surgical scalpels are well known devices used by surgeons and other medical personnel to make incisions into patients. These scalpels consist of a handle member, typically made of steel, and a removable surgical blade disposed on one end of the handle. The surgical blades must be extremely sharp and made from surgical stainless steel, e.g., a grade of stainless steel suitable for biomedical applications. So called surgical steels may include austenitic SAE 316 stainless and martensitic SAE 440, SAE 420, and 17-4 stainless steels, or other grade of corrosion resistant steel. Surgical blades must be handled carefully by all personnel involved in the surgical procedure in which the scalpel is used.

Previously retractable surgical blade have been disclosed that provide protection to medical personnel from stabbing and cutting by scalpels during surgical procedures. The devices provided a handle in which the cutting edge of a blade could be retracted when not in use. Such devices required a feature such as a projection or snap-on for attaching the steel cutting blade. This resulted in additional components to be assembled and further risk of cutting and/or stabbing in the assembly process, as well as increased cost due to the surgical grade steel blade.

Clearly, there is a need for an improved surgical blade device that requires fewer parts fabricated from inexpensive materials, to reduce injury and costs in manufacturing.

What is needed is a system and/or method that satisfies one or more of these needs or provides other advantageous features. Other features and advantages will be made apparent from the present specification. The teachings disclosed extend to those embodiments that fall within the scope of the claims, regardless of whether they accomplish one or more of the aforementioned needs.

SUMMARY

One embodiment relates to a surgical device that comprises a handle defining a channel and a surgical blade member having a body member and a surgical plastic blade member integrally formed therewith. The body member has a portion which engages the channel so that the surgical plastic blade member can move between (a) a cutting position in which the surgical blade projects from the handle to perform a surgical procedure and (b) a retracted position in which the surgical blade is disposed in the channel. When in the retracted position, the surgical plastic blade member is prevented from contact with users performing the surgical procedure. The device further includes cooperating locking members on the handle and the body member to position and secure the device in the desired position.

Another embodiment relates to a method of providing a retractable surgical device as described above in the retracted position and moving the integral surgical plastic blade member into the cutting position. A surgical procedure is then performed. The surgical plastic blade member is then moved from the cutting position back into the retracted position.

An object of the invention is to provide a unitary surgical plastic blade member and sliding grip projection which greatly reduces the incidence of inadvertent stabbing and cutting of medical personnel during surgical procedures.

It is an object of the invention to provide a surgical blade device which greatly reduces the incidence of inadvertent stabbing and cutting of medical personnel during surgical procedures.

It is a further object of the invention to provide a surgical blade device that is easy to use.

It is still a further object of the invention to provide a surgical blade device that can be safely disposed of after the surgical procedure is completed.

It is yet another object of the invention to provide a surgical blade device that has a surgical blade body member that can be placed in numerous positions in the handle of the device.

It is still another object of the invention to provide a surgical plastic blade member that is formed with an integral edge by laser, rapid prototyping, stereolithography, and similar techniques that is integrated with an engaging surface for slidably moving the blade to and from the retracted position. Materials for forming the surgical plastic blade member include thermoplastic, polypropylene, Acrylonitrile butadiene styrene (ABS), glass-filled polycarbonate, and other resins or ceramic materials having hardness and sharpening properties suitable for surgical cutting.

It is still yet another object of the invention to provide a method of performing a surgical procedure using a retractable surgical blade device.

These and other objects of the invention will be more fully understood from the following description of the invention with reference to the drawings appended hereto . . . .

Alternative exemplary embodiments relate to other features and combinations of features as may be generally recited in the claims.

BRIEF DESCRIPTION OF THE FIGURES

The application will become more fully understood from the following detailed description, taken in conjunction with the accompanying figures, wherein like reference numerals refer to like elements, in which:

FIG. 1 is an elevational view of an embodiment of a retractable surgical blade device made in accordance with the invention.

FIG. 2 is a cross-sectional view taken along line 2-2 of FIG. 1.

FIG. 3 is a cross-sectional view taken along line 3-3 of FIG. 1.

FIG. 7 is a perspective view showing an embodiment of the stop means of the invention which comprises a cantilevered section of the flange of the handle before the cantilevered section is crimped to form stop means.

FIG. 8 is an end view of the embodiment of FIG. 7 only showing the cantilevered section in its crimped position.

DETAILED DESCRIPTION OF THE EXEMPLARY EMBODIMENTS

Figure 4:
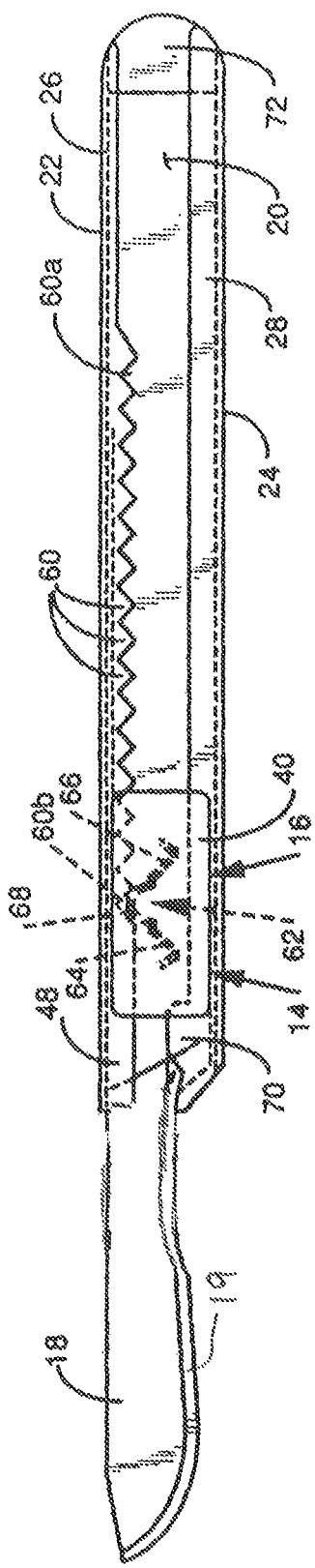
FIG. 4 is an elevational view showing the retractable surgical blade device in the cutting position.

Before turning to the figures which illustrate the exemplary embodiments in detail, it should be understood that the application is not limited to the details or methodology set forth in the following description or illustrated in the figures. It should also be understood that the phraseology and terminology employed herein is for the purpose of description only and should not be regarded as limiting.

Referring now to FIGS. 1-3, a retractable surgical blade device 10 made in accordance with the invention is shown. The device 10 consists of a handle member 12 and surgical blade member 14 which is adapted for slidable movement in the handle member 12. The surgical blade member 14 further consists of a body member 16 having a distal end formed into a surgical blade 18 with an edge 19 suitable for cutting. Blade 18 may be made of plastic material, which may be formed with an integral edge by laser, rapid prototyping, and similar techniques, to create a sharpened edge 19 that is integral with the entire plastic surgical blade member including the sliding grip portion.

The handle member 12 consists of a base wall 20, two elongated generally parallel longitudinal sidewalls 22 and 24 which extend generally perpendicularly from the longitudinal edges of the base wall 20 and two elongated longitudinal flanges 26 and 28 which extend generally perpendicularly from the longitudinal edges of the respective sidewalls 22 and 24. The handle member 12, therefore, defines a channel 30 (FIG. 3) in which the surgical blade member 14 is slidably movable. It will be appreciated that the handle member 12 can be made of any suitable material, such as steel or plastic, and can be either for a one-time use (disposable) or for multiple uses.

As can best be seen in FIG. 3, the body member 16 has a cross-sectional shape of an "I-beam" consisting of a top portion 40, a bottom portion 42 and an interconnecting intermediate portion 44. The body member 16 shape defines a pair of opposed longitudinal slots 45, 46. Flanges 26 and 28 engage into slots 45, 46 respectively and cooperate to guide and maintain the surgical blade member 14 in the channel 30. The bottom portion 42 is disposed in the channel 30, while top portion 40 includes an engaging section which extends above the handle member 12 to facilitate grasping and moving the surgical blade member 14 in the channel 30. The engaging section has an engaging surface 47 which is preferably serrated in order to further enhance the users grip on the body member 16 of the surgical blade member 14. It will be appreciated that the body member 16 can be made of any suitable material such as steel or plastic and can also be designed for one-time (disposable) use or multiple uses.

The surgical blade 18 transitions into a flange portion 48 of the body member 16 as can best be seen in FIGS. 1 and 2.

The surgical blade member 14 is shown in FIG. 1 in its "retracted position". In this position, the surgical blade member 14 is retracted entirely into channel 30 thus edge 19 and surgical blade 18 are not exposed. While in the retracted position, the device 10 can be handled by medical personnel and others and can be stored without the danger of the surgical blade 18 causing a stab or other type of wound. In addition, once the device 10 is disposed of when in the retracted position, waste processing personnel are also protected against inadvertent stab or cut wounds.

The surgical blade member 14 is held in the retracted position by cooperating locking members on the handle member 12 and the body member 16 of surgical blade member 14. The locking members consist of a plurality of notches 60 formed into flange 26 and resilient spring clip member 62, shown in phantom line drawing in FIG. 1, which engages into the notches 60 to prevent sliding movement of the surgical blade member 14 when it is placed in the desired position. The spring clip member 62 has two end portions 64 and 66 which are embedded in the body member 16 (FIGS. 1 and 2) and a projecting portion 68 which projects from the interconnecting intermediate portion 44 of the body member 16 as can best be seen in FIG. 3. The projecting portion 68 engages into notch 60a to hold the surgical blade member 14 in the retracted position as is shown in FIG. 1.

It will be appreciated that the surgical blade member 14 can be placed into discrete positions between the cutting position and the retracted position by disposing the projection 68 in the intermediate notches 60 between notches 60a and 60b.

In operation, when it is desired to use the device 10 in a surgical procedure, the engaging surface 47 is grasped preferably by a user's thumb and the surgical blade member 14 is extended to a "cutting position" shown in FIG. 4. In the cutting position, the surgical blade 18 is exposed and ready for use in a surgical procedure. It will be appreciated that the surgical blade member 14 slidably moves from the retracted position shown in FIG. 1 to the cutting position shown in FIG. 4 by the user applying a force on the surgical blade member 14 to translate the surgical blade member 14 in the channel 30. The spring clip member 62, because of its resilience, slides over the intermediate notches until it reaches notch 60b. Notch 60b and the projecting portion 68 of the spring clip member 62 position and lock the surgical blade member 16 in the cutting position.

As used herein, the term "surgical procedure" means a procedure involving an incision performed by medical personnel, including doctors, nurses, emergency medical technicians and other paraprofessionals, on a human or animal patient wanting or needing medical assistance in a hospital, doctor's office, or other location where medical attention is needed or desired, such as an accident scene.

The device 10 also has stop means located at both ends thereof. One of the stop means consists of an extension section 70 of flange 28. As can be seen in FIG. 4, when the surgical blade member 14 is in the cutting position, the body member 16 abuts extension section 70 to prevent further leftward movement (FIG. 4) of the surgical blade member 14. This prevents the surgical blade member 14 from disengaging from the handle member 12 at the left end of the handle member 12. Another stop means is provided on the other end of the handle member 12. This stop means consists of a plug 72 which fits into the channel 30 at the right most end of the handle member 12. This prevents the surgical blade member 14 from disengaging from the handle member 12 at the right end of the handle member 12.

When the surgical procedure is completed, the user merely slides the surgical blade member 14 back into the retracted position. At this point, if desired, the entire device 10 can be disposed of or the surgical blade member 14 can be removed after removing plug 72.

Figure 5:
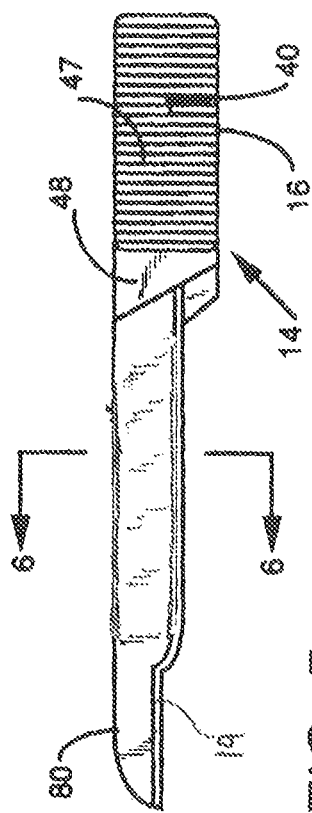
FIG. 5 is an elevational view of the surgical blade member showing a different surgical blade.
Figure 6:
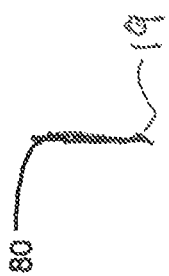
FIG. 6 is a cross-sectional view taken along line 6-6 of FIG. 5.

FIGS. 5 and 6 shows another embodiment of a surgical blade member in which like parts of surgical blade member 16 are labelled with like reference characters. The surgical blade member 16 of FIG. 5 has a surgical blade 80 configured differently than shown in FIGS. 1-4. As can be seen in FIG. 6, the blade 80 is narrower toward the distal tip with a straight cutting edge 19, rather than the slightly curved blade 18. It will be appreciated that the invention contemplates utilizing various shapes of surgical blade.

As was mentioned above, the entire device 10 can be made for a one-time use in which the device 10 is used for a surgical procedure and, after being placed in the retracted position, is then disposed of properly. In this case, the device 10 can be packaged in a sterile sealed package 10', as shown in FIG. 7, which is opened when it is desired to use the device 10. It will be appreciated that instead of properly disposing the entire device 10, as is preferred, the surgical blade member 14 only can be removed from the handle member 12 and disposed of properly.

FIG. 7 shows another embodiment of the stop means of the invention. Instead of plug 72, flange 26 has a cantilevered end portion 84 shown in phantom in FIG. 7 that can be crimped to form a crimped section 84' as shown in solid line on FIG. 7 and as can been seen also in FIG. 8. In this way, the crimped section 84' prevents the surgical blade member 14 from becoming accidentally disengaged from the handle member 12 of the right end of the handle member 12, similarly to plug 72. If desired, crimped section 84' can be straightened such as by using pliers or other hand tools so that the surgical blade member 14 can be removed from the handle member 12.

The method of the invention involves providing the retractable surgical blade device 10 as described above in the retracted position and then moving the surgical blade member 14 into a cutting position in which the surgical blade 18 projects from the handle 12. Once in the cutting position, an incision is made into the patient and a surgical procedure is performed. After performing the surgical procedure, the surgical blade member 14 is moved into the retracted position so that the surgical blade is unable to cut or stab persons associated with a surgical procedure.

The device 10 shown in FIGS. 1-8 is preferably grasped by a user's right hand so that the user's thumb can engage the engaging surface 47 to move the surgical blade member 14 in the channel 30. The invention contemplates also a "left hander's" version of the device, which is essentially a mirror image of device 10, such that the device can be grasped and used efficiently with a user's left hand.

The surgical plastic blade member 14 is formed with an integral edge by various methods, e.g., laser, rapid prototyping, stereolithography, and similar techniques. The plastic blade member may be integrated with an engaging surface 47 for slidably manipulating the blade to and from the retracted position. Materials for forming the surgical plastic blade member include thermoplastic, polypropylene, Acrylonitrile butadiene styrene (ABS), glass-filled polycarbonate, and other resins or ceramic materials having hardness and sharpening properties suitable for surgical cutting. Plastic blade member may also be formed by injection molding, thermoforming, CNC, and other similar methods.

It will be appreciated that a retractable surgical blade device and an associated method of performing a surgical procedure are provided which greatly reduces the incidence of inadvertent stab or cut wounds to medical personnel and others involved in handling the device.

While the exemplary embodiments illustrated in the figures and described herein are presently preferred, it should be understood that these embodiments are offered by way of example only. Accordingly, the present application is not limited to a particular embodiment, but extends to various modifications that nevertheless fall within the scope of the appended claims. The order or sequence of any processes or method steps may be varied or re-sequenced according to alternative embodiments.

It is important to note that the construction and arrangement of the retractable scalpel with unitary sliding plastic blade, as shown in the various exemplary embodiments is illustrative only. Although only a few embodiments have been described in detail in this disclosure, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter recited in the claims. For example, elements shown as integrally formed may be constructed of multiple parts or elements, the position of elements may be reversed or otherwise varied, and the nature or number of discrete elements or positions may be altered or varied. Accordingly, all such modifications are intended to be included within the scope of the present application. The order or sequence of any process or method steps may be varied or re-sequenced according to alternative embodiments. In the claims, any means-plus-function clause is intended to cover the structures described herein as performing the recited function and not only structural equivalents but also equivalent structures. Other substitutions, modifications, changes and omissions may be made in the design, operating conditions and arrangement of the exemplary embodiments without departing from the scope of the present application.

It should be noted that although the figures herein may show a specific order of method steps, it is understood that the order of these steps may differ from what is depicted. Also two or more steps may be performed concurrently or with partial concurrence. Such variation will depend on the software and hardware systems chosen and on designer choice. It is understood that all such variations are within the scope of the application. Likewise, software implementations could be accomplished with standard programming techniques with rule based logic and other logic to accomplish the various connection steps, processing steps, comparison steps and decision steps.

What is claimed is:

1. A retractable surgical blade device comprising:
   a handle having a front end and a back end, said handle including a base wall and a pair of opposed sidewalls extending generally perpendicularly from said base wall, said sidewalls each including a flange extending generally perpendicularly therefrom;
   said base wall, said sidewalls and said flanges defining a channel;
   a surgical blade member comprising a body member which defines a pair of opposed longitudinal slots and a blade portion integrally formed with said body member as a monolithic piece, the blade portion having a cutting edge; said blade portion being non-detachable from said body member and comprising an integral cutting edge formed by laser, rapid prototyping, or stereolithography;
   said flanges engaging into said slots to guide and maintain said surgical blade member in said channel;
   said surgical blade member being movable between a cutting position wherein said blade portion projects from said front end of said handle and said device can be employed in a surgical procedure and a retracted position wherein said-blade portion is disposed in said channel so that said blade portion is unable to cut or stab persons associated with a surgical procedure;

said handle includes a front end stop comprising a section extending from said flange to resist said surgical blade member from disengaging from said front end of said handle and a back end stop comprising a crimped cantilevered end portion to resist said surgical blade member from disengaging from said back end of said handle; and said device further including cooperating locking members on said handle and said body member, said locking members positioning and securing said blade portion in a desired position.

2. The device of claim 1, wherein said surgical blade member is slidably movable in said channel between said retracted position and said cutting position.

3. The device of claim 1, wherein said cooperating locking members include at least two notches in one of said flanges and a resilient spring clip member on said body member adapted to engage into said notches, wherein said resilient spring clip member engages into a first said notch when said surgical blade member is in said cutting position and said resilient spring clip member engages into a second said notch when said surgical blade member is in said retracted position.

4. The device of claim 3, wherein said resilient spring clip member on said body member to engage into said notches is a resilient spring clip having two ends and an intermediate portion disposed between said two ends; and each of said ends is secured to a respective portion of said body member and said intermediate portion projects from said body member to engage into said notches.

5. The device of claim 4, wherein said handle includes a plurality of notches in addition to said first and second notches for positioning said surgical blade member in positions between said cutting position and said retracted position.

6. The device of claim 1, wherein said body member includes an engaging section, said engaging section being employed to move said surgical blade member in said channel.

7. The device of claim 6, wherein said engaging section includes an engaging surface having serrations in order to facilitate gripping thereof.

8. The device of claim 1, wherein said handle is made of materials selected from the group consisting of metal and plastic.

9. The device of claim 1, wherein said body member is made of materials selected from the group consisting of metal and plastic.

10. The device of claim 1, wherein said handle includes two generally parallel elongated sidewalls.

11. A method of performing a surgical procedure comprising:

providing a retractable surgical blade device comprising (i) a handle having a front end and a back end, said handle including a base wall and a pair of opposed sidewalls extending generally perpendicularly from said base wall, said sidewalls each including a flange extending generally perpendicularly therefrom wherein said base wall, said sidewalls and said flanges define a channel; (ii) a surgical blade member having a body member which defines a pair of opposed longitudinal slots and a blade portion integrally formed as a monolithic piece at a distal end of said body member, said blade portion being non-detachable from said body member and comprising an integral cutting edge formed by laser, rapid prototyping, or stereolithography; said flanges engaging into said slots to guide and maintain said surgical blade member in said channel; and (iii) said handle includes a front end stop comprising a section extending from said flange to resist said surgical blade member from disengaging from said front end of said handle and a back end stop comprising a cantilevered end portion that is crimped to resist said surgical blade member from disengaging from said back end of said handle;

providing said device being in a retracted position wherein said blade portion is disposed in said channel;

moving said surgical blade member into a cutting position wherein said surgical blade projects from said front end of said handle;

performing a surgical procedure using said device while said surgical blade member is in said cutting position; and moving said surgical blade member back into said retracted position wherein said blade portion is retracted into said channel such that said blade portion is unable to cut or stab persons associated with a surgical procedure.

12. The method of claim 11, including after retracting said surgical blade member into said retracted position, disposing of said device.

13. The method of claim 11, including storing said device in said retracted position.

\* \* \* \* \*